US005517993A

United States Patent [19]
Unger et al.

[11] Patent Number: 5,517,993
[45] Date of Patent: May 21, 1996

[54] COPOLYMERS AND THEIR USE AS CONTRAST AGENTS IN MAGNETIC RESONANCE IMAGING AND IN OTHER APPLICATIONS

[75] Inventors: Evan C. Unger; Guanli Wu, both of Tucson, Ariz.

[73] Assignee: ImaRx Pharmaceutical Corp., Tucson, Ariz.

[21] Appl. No.: 477,936

[22] Filed: Jun. 7, 1995

Related U.S. Application Data

[62] Division of Ser. No. 305,257, Sep. 14, 1994, Pat. No. 5,458,127, which is a division of Ser. No. 949,691, Sep. 22, 1992, Pat. No. 5,385,719, which is a continuation-in-part of Ser. No. 765,921, Sep. 24, 1991, abandoned.

[51] Int. Cl.$^6$ .................................................. A61B 5/05
[52] U.S. Cl. ...................... 128/653.4; 528/272; 528/275; 528/277; 528/280; 528/296; 528/302; 528/332; 528/350; 528/351; 528/353; 528/367; 562/623; 556/1; 534/16; 424/9.341; 424/9.35; 424/9.36
[58] Field of Search ..................... 528/272, 275, 528/277, 280, 96, 302, 332, 350, 351, 353, 367; 562/623; 556/1; 534/16; 424/9.341, 9.35, 9.36; 436/173, 808; 128/653.2, 653.4, 654

[56] References Cited

U.S. PATENT DOCUMENTS

| | | | |
|---|---|---|---|
| 2,831,885 | 4/1958 | Kroll et al. | 556/148 |
| 3,058,948 | 10/1962 | Mosimann et al. | 525/504 |
| 3,859,337 | 1/1975 | Herz et al. | 562/623 |
| 4,457,870 | 7/1984 | Schröder et al. | 556/50 |
| 4,647,447 | 3/1987 | Gries et al. | 424/9 |
| 4,687,658 | 8/1987 | Quay | 424/9 |
| 4,687,659 | 8/1987 | Quay | 424/9 |
| 4,729,892 | 3/1988 | Beall | 424/9 |
| 4,730,066 | 3/1988 | White | 556/50 |
| 4,746,507 | 5/1988 | Quay | 424/9 |
| 4,822,594 | 4/1989 | Gibby | 424/9 |
| 4,826,673 | 5/1989 | Dean et al. | 424/9 |
| 4,830,716 | 5/1989 | Ashmead | 204/72 |
| 4,885,363 | 12/1989 | Tweedle et al. | 540/465 |
| 4,888,032 | 12/1989 | Busch | 55/38 |
| 4,916,246 | 4/1990 | Felder et al. | 556/1 |
| 4,933,441 | 6/1990 | Gibby | 536/112 |
| 4,933,456 | 6/1990 | Rocklage et al. | 546/5 |
| 4,935,518 | 6/1990 | Rocklage et al. | 546/6 |
| 4,952,289 | 8/1990 | Ciccone et al. | 204/129 |
| 4,963,344 | 10/1990 | Gries et al. | 424/9 |
| 4,978,763 | 12/1990 | Rocklage et al. | 556/50 |

FOREIGN PATENT DOCUMENTS

| | | |
|---|---|---|
| 2193095 | 2/1988 | United Kingdom . |
| 90/01792 | 5/1991 | WIPO . |

OTHER PUBLICATIONS

Runge, et al., "Paramagnetic Contrast Agents in Magnetic Resonance Imaging: Research at Vanderbilt University", *Physiol. Chem. Phys. Med. NMR*, (1984), 16, 113–122.

Tscholakoff, et al., "MR Imaging in the Diagnosis of Pancreatic Disease", *AJR*, (1987), 148, 703–709.

Wesbey, et al., "Nuclear Magnetic Resonance Contrast Enhancement Study of the Gastrointestinal Tract of Rats and a Human Volunteer using Nontoxic Oral Iron Solutions", *Radiology*, (1983), 149, 175–180.

Wesbey, et al., "Dilute Oral Iron Solutions as Gastrointestinal Contrast Agents for Magnetic Resonance Imaging; Initial Clinical Experience", *Magn. Reson. Imaging*, (1985), 3, 57–64.

Weinreb, et al., "Improved MR Imaging of the Upper Abdomen with Glucagon and Gas", *J. Comput. Assist. Tomogr.*, 8, (1984), 835–838.

Widder, et al., "Magnetite Albumin Suspension: A Superparamagnetic Oral MR Contrast Agent", *AJR*, (1987), 149, 839–843.

Williams, et al., "Nonabsorbable Iron Preparations as Gastrointestinal Contrast Agents for MR Imaging: Preliminary Investigations", *Radiology*, (1986), 161, 315.

Young, et al., "Enhancement of Relaxation Rate with Paramagnetic Contrast Agents in NMR Imaging", *CT*, (1981), 5, 543.

Clanton, et al., "The Use of Oral Contract and Respiratory Gating in MR Imaging of the Pancrease", *Radiology*, (1984), 153, 159.

Clanton, et al., "Techniques Employees in NMR Imaging Using Oral Contrast Agents", *Radiology*, (1983), 149, 238.

(List continued on next page.)

*Primary Examiner*—Samuel A. Acquah
*Attorney, Agent, or Firm*—Woodcock Washburn Kurtz Mackiewicz & Norris

[57] ABSTRACT

Novel compounds having use as contrast agents in magnetic resonance imaging, as well as other uses, are described. The compounds are comprised of a copolymer which comprises at least two of a first monomer of the formula $X_1\text{-}(CHR_2CHR_2\text{—}Y)_n\text{—}(CHR_2)_m\text{—}CHR_2CHR_2\text{—}X_2$, wherein $X_1$ and $X_2$ are, independently, OH, $NH_2$, $NHR_1$, COOH, $COOR_1$, SH, or Z, Y is O, NH, $NR_1$, S, or CO, n is 0–10,000, m is 0 or 1, each Z is, independently, Cl, Br, or I, each $R_1$ is, independently, a $C_1$–$C_{20}$ substituted alkyl or cycloalkyl, and each $R_2$ is, independently, H or OH, and at least one of a second monomer which is a polynitrilo chelating agent having at least two COOH, $COOR_1$, or COZ groups, the first and second monomers being bound to one another to form a copolymer through an ester, amide, or carboxylic thioester linkage of at least one of the OH, $NH_2$, $NHR_1$, COOH, $COOR_1$, SH or Z groups of the first monomer, and at least one of the COOH, $COOR_1$, or COZ groups of the second monomer. Optionally, the copolymer may also include at least one of a third monomer which is a targeting agent or a targeting agent ligand having an OH, $NH_2$, $NHR_1$, COOH, $COOR_1$, SH, or COZ group, wherein $R_1$ is described as above, and wherein the third monomer is also bound with the first and second monomers to form a copolymer through an ester, amide, or carboxylic thioester linkage. For magnetic resonance imaging, for example, the copolymer may further comprise a paramagnetic ion chelated to the chelating agent.

16 Claims, No Drawings

OTHER PUBLICATIONS

Hahn, et al., "Imaging Artifacts Introduced by NRI Gastrointestinal Contrast Agents: Magnitude, Cause and Amelioration", *Magn. Reson. Imaging*, (1988), 6, 78.

Hahn, et al., "Ferrite Particles for Bowel Contrast in MR Imaging: Design Issues and Feasibility Studies", *Radiology*, (1987), 164, 37–41.

Kornmesser, et al., "Gastrointestinal Contrast Enhancement in MRI: First Clinical Experience with Gadolinium–DTPA", *Magn. Reson. Imaging*, (1988) 6, 124.

Laniado, et al., "MR Imaging of the Gastrointestinal Tract: Value of Gd–DTPA", *AJR*, (1988), 150, 817–821.

Mattrey, et al., "Perfluorochemicals as Gastrointestinal Contrast Agents for MR Imaging", *AJR*, (1988), 148, 1259–1263.

Newhouse, et al., "NMR Imaging Preliminary Results in the Upper Extremities of man and the Abdomen of Small Animals", *Radiology*, (1982), 142, 246.

Runge, et al., "Work in Progress: Potential Oral and Intravenous Paramagnetic NMR Contrast Agents[1]", *Radiology*, (1983), 147, 789–791.

COPOLYMERS AND THEIR USE AS CONTRAST AGENTS IN MAGNETIC RESONANCE IMAGING AND IN OTHER APPLICATIONS

This is a divisional of application Ser. No. 305,257, filed Sep. 14, 1994, U.S. Pat. No. 5,453,127 which in turn is a divisional of application Ser. No. 949,691, filed Sep. 22, 1992, now U.S. Pat. No. 5,385,719, which in turn is a continuation-in-part application Ser. No. 765,921, filed Sep. 24, 1991, abandoned.

BACKGROUND OF THE INVENTION

1. Field of the Invention

This invention relates to novel compounds useful as contrast agents for magnetic resonance imaging, and in other diagnostic and therapeutic applications.

2. Description of the Prior Art

There are a variety of imaging techniques that have been used to diagnose disease in humans. One of the first imaging techniques employed was X-rays. In X-rays, the images produced of the patients' body reflect the different densities of body structures. To improve the diagnostic utility of this imaging technique, contrast agents are employed to increase the density between various structures, such as between the gastrointestinal tract and its surrounding tissues. Barium and iodinated contrast media, for example, are used extensively for X-ray gastrointestinal studies to visualize the esophagus, stomach, intestines and rectum. Likewise, these contrast agents are used for X-ray computed tomographic studies to improve visualization of the gastrointestinal tract and to provide, for example, a contrast between the tract and the structures adjacent to it, such as the vessels or lymph nodes. Such gastrointestinal contrast agents permit one to increase the density inside the esophagus, stomach, intestines and rectum, and allow differentiation of the gastrointestinal system from surrounding structures.

Magnetic resonance imaging (MRI) is a relatively new imaging technique which, unlike X-rays, does not utilize ionizing radiation. Like computed tomography, MRI can make cross-sectional images of the body, however MRI has the additional advantage of being able to make images in any scan plane (i.e., axial, coronal, sagittal or orthogonal). Unfortunately, the full utility of MRI as a diagnostic modality for the body, particularly in the abdominal and pelvic region, is hampered by the lack of an effective gastrointestinal contrast agent. Without such an agent, it is often difficult using MRI to differentiate the intestines from, for example, adjacent soft tissues and lymph nodes. If better contrast agents were available, the overall usefulness of MRI as an imaging agent would improve, and the diagnostic accuracy of this modality in the gastrointestinal region would be greatly enhanced.

MRI employs a magnetic field, radiofrequency energy and magnetic field gradients to make images of the body. The contrast or signal intensity differences between tissues mainly reflect the T1 and T2 relaxation values and the proton density (effectively, the free water content) of the tissues. In changing the signal intensity in a region of a patient by the use of a contrast medium, several possible approaches are available. For example, a contrast medium could be designed to change either the T1, the T2 or the proton density.

A paramagnetic contrast agent such as Gd-DTPA causes longitudinal relaxation to shorten T1. This increases the signal intensity on T1-weighted images. A superparamagnetic contrast agent such as ferrites works predominantly on transverse relaxation causing a shortening of T2 and decreasing signal intensity on T2-weighted images. A contrast agent could also work by altering the proton density, specifically by decreasing the amount of free water available that gives rise to the signal intensity.

Agents that increase the signal intensity from the lumen compared to the native contents are termed positive contrast agents. A number of these have been examined as contrast agents for MRI. These include fats and oils (Newhouse et al., *Radiology,* 142(P):246 (1982)), which increase signal as a result of their short T1, long T2 and high intrinsic proton density, as well as various paramagnetic agents that increase signal by decreasing the T1 of water protons. Examples of such paramagnetic agents include Gd-DTPA (Kornmesser et al., *Magn. Reson. Imaging,* 6:124 (1988), and Laniado et al., *AJB,* 150:817 (1988)), Gd-DOTA (Hahn et al. *Magn. Reson. Imaging,* 6:78 (1988)), Gd-oxalate (Runge, V. M. et al., *Radiology,* 147:789 (1983)), Cr-EDTA (Runge, V. M. et al., *Physiol. Chem. Phys. Med. NMR,* 16:113 (1984)), Cr-Tris-acetylacetonate (Clanton et al., *Radiology,* 149:238 (1983)), ferric chloride (Young et al., *CT,* 5:543 (1981)), ferrous gluconate (Clanton et al., *Radiology,* 153:159 (1984)), ferric ammonium citrate and ferrous sulfate (Wesbey et al., *Radiology,* 149:175 (1983) and Tscholakoff et al., *AJR,* 148:703 (1987)) as well as iron complexes (Wesbey et al., *Magn. Reson. Imaging,* 3:57 (1985), and Williams et al., *Radiology,* 161:315 (1986)). Other paramagnetic contrast agents include saccharides or reduced lower carbohydrates bound to a compound coordinated with a paramagnetic ion (Gibby, U.S. Pat. No. 4,933,441, and Gibby, U.S. Pat. No. 4,822, 594), and liposomes entrapping paramagnetic ions (U.K. Patent Application GB 2193095).

Alternatively, agents that decrease the signal intensity from the lumen are termed negative contrast agents. Examples include particulate iron oxides (Hahn et al., *Radiology,* 164:37 (1987), Widder et al., *AJR,* 149:839 (1987)) which decrease signal via T2 shortening, as well as gas-evolving materials (Weinreb et al., *J. Comput. Assist. Tomogr.,* 8:835 (1984)) and perfluorocarbons (Mattrey et al., *AJR,* 148:1259 (1987)) which act through changes in the proton density. It should be recognized that all paramagnetic substances at sufficiently high concentrations can also result in a decrease in signal intensity via T2 shortening.

The existing MRI contrast agents all suffer from a number of limitations, including problems with stability, degradation, relaxivity, signal intensity, biodistribution, toxicity, antigenicity and/or cost. For example, liposomes containing paramagnetic ions have the disadvantage that the lipid may oxidize in storage and, furthermore, the lipid itself may be quite expensive to employ. With saccharides or reduced lower carbohydrates bound to a compound coordinated to a paramagnetic ion, stability is a problem, and decomplexation and unfavorable biodistribution of the paramagnetic ion results.

New and/or better contrast agents useful in magnetic resonance imaging are needed. The present invention is directed to this, as well as other, important ends.

SUMMARY OF THE INVENTION

The present invention is directed to compounds useful, inter alia, in magnetic resonance imaging, the compounds comprising a copolymer which includes at least two of a first monomer of the formula [I]

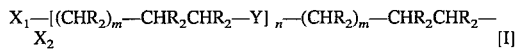

[I]

wherein $X_1$ and $X_2$ are, independently, OH, $NH_2$, $NHR_1$, COOH, $COOR_1$, SH, or Z, Y is O, NH, $NR_1$, S, or CO, each Z is, independently, Cl, Br, or I, n is 0–10,000, each m is 0 or 1, each $R_1$ is, independently, a $C_1$–$C_{20}$ substituted or unsubstituted alkyl or cycloalkyl group, and each $R_3$ is, independently, H or OH, and at least one of a second monomer which is a polynitrilo chelating agent having at least two COOH, $COOR_1$, or COZ groups, wherein Z and $R_1$ are as described above, the first and second monomers bound to one another to form a copolymer through an ester, amide, or carboxylic thioester linkage of at least one of the OH, $NH_2$, $NHR_1$, COOH, $COOR_1$, SH, or Z groups of the first monomer and at least one of the COOH, $COOR_1$, or COZ groups of the second monomer. For use in magnetic resonance imaging, for example, the compounds further comprise a paramagnetic ion chelated to the chelating agent in the copolymer.

The present invention is also directed to compounds useful, inter alia, in magnetic resonance imaging, the compounds comprising a copolymer which includes at least two of a first monomer of the formula [I]

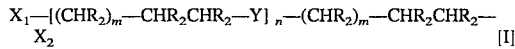

[I]

wherein $X_1$ and $X_2$ are, independently, OH, $NH_2$, $NHR_1$, COOH, $COOR_1$, SH, or Z, Y is O, NH, $NR_1$, S, or CO, each Z is, independently, Cl, Br, or I, n is 0–10,000, each m is 0 or 1, each $R_1$ is, independently, a $C_1$–$C_{20}$ substituted or unsubstituted alkyl or cycloalkyl group, and each $R_2$ is, independently, H or OH, and at least one of a second monomer which is a polynitrilo chelating agent having at least two COOH, $COOR_1$, or COZ groups, wherein Z and $R_1$ are as described above, and at least one of a third monomer which is a targeting agent having an OH, $NH_2$, $NHR_1$, COOH, $COOR_1$, SH, or COZ group, wherein Z and $R_1$ are as described above, the first, second, and third monomers bound to one another to form a copolymer through an ester, amide, or carboxylic thioester linkage of at least one of the OH, $NH_2$, $NHR_1$, COOH, $COOR_1$, SH, or Z groups of the first monomer, at least one of the COOH, $COOR_1$, or COZ groups of the second monomer, and at least one of the OH, $NH_2$, $NHR_1$, COOH, $COOR_1$, SH, or COZ groups of the third monomer. For use in magnetic resonance imaging, for example, the compounds further comprise a paramagnetic ion chelated to the chelating agent.

Also preferable are compounds comprising a copolymer which includes at least two of a first monomer of the formula HS-$[(CHR_2)_m$—$CHR_2CHR_2$—Y$]_n$— $(CHR_2)_m$—$CHR_2CHR_2$—SH, wherein Y is O, NH, $NR_1$, S, or CO, n is 0–10,000, each m is 0 or 1, each $R_1$ is, independently, a $C_1$–$C_{20}$ substituted or unsubstituted alkyl or cycloalkyl group, and each $R_2$ is, independently, H or OH, and at least one of a second monomer which is a polynitrilo chelating agent having at least two COOH, $COOR_1$, or COZ groups, wherein $R_1$ is as described above, and wherein each Z is, independently, Cl, Br, or I, the first and second monomers bound to one another to form a copolymer through a carboxylic thioester linkage of at least one of the SH groups of the first monomer and at least one of the COOH, $COOR_1$, or COZ groups of the second monomer. For use in magnetic resonance imaging, for example, these preferred compounds further comprise a paramagnetic ion chelated to the chelating agent.

Also preferred are compounds comprising a copolymer which includes at least two of a first monomer of the formula HS-$[(CHR_2)_m$—$CHR_2CHR_2$—Y$]_n$— $(CHR_2)_m$—$CHR_2CHR_2$—SH, wherein Y is O, NH, $NR_1$, S, or CO, n is 0–10,000, and each m is 0 or 1, each $R_1$ is, independently, a $C_1$–$C_{20}$ substituted or unsubstituted alkyl or cycloalkyl group, and each $R_2$ is, independently, H or OH, and at least one of a second monomer which is a polynitrilo chelating agent having at least two COOH, $COOR_1$, or COZ groups, wherein $R_1$ is as described above and each Z is, independently, Cl, Br, or I, and at least one of a third monomer which is a targeting agent, said targeting agent having an OH, $NH_2$, $NHR_1$, COOH, $COOR_1$, SH, or COZ group, wherein $R_1$ and Z are as described above, said first, second, and third monomers bound to one another to form a copolymer through an ester, amide, or carboxylic thioester linkage of at least one of said SH groups of said first monomer, at least one of said COOH, $COOR_1$, or COZ groups of said second monomer, and at least one of said OH, $NH_2$, $NHR_1$, COOH, $COOR_1$, SH, or COZ groups of said third monomer. For use in magnetic resonance imaging, for example, these preferred compounds further comprise a paramagnetic ion chelated to the chelating agent.

In place of the first monomer of formula [I], one can employ monomers such as, for example, 1,3-diaminopropane, 1,4-diaminobutane, 1,5-diamino-3-(2-aminoethyl)-pentane, N,N'-dimethyl-1,2,-diaminopropane, 2-hydroxy-1,3-diaminopropane, 2-amino-1,3-diaminopropane, 2,3-diamino-1,4-butanediol, 1,4-diamino-2,3-butanediol, 1,4-diaminocyclohexane, 1,4-phenylenediamine, 1,1,1-tris(aminomethyl)ethane, 2,2',2"-triaminotriethylamine, tris-(aminomethyl)methane, 1,3,5-triaminocyclohexane, 1,3,5-phenylenetriamine, 2,2-dimethyl-1,3-propanediol, tris(2-hydroxyethyl)amine, 1,1,1-tris(hydroxymethyl)ethane, and tris(hydroxymethyl)-aminomethane, and the like.

For reasons of increased diagnostic effectiveness, it is preferable that the first and second monomers of the copolymer (and the third monomers, where third monomers are included) comprise, collectively, at least about 10 monomers, more preferably at least about 20 monomers, even more preferably at least about 50 monomers, still more preferably at least about 100 monomers, and most preferably at least about 150 monomers, preferably up to about 400, more preferably up to about 350, even more preferably up to about 300, still more preferably up to about 250 monomers, and most preferably up to about 200 monomers, although the number of monomers, may if desired, range up to about 500, 1000, 2000, etc.

The subject invention also pertains to a method of providing an image of an internal region of a patient the method comprising (i) administering to the patient one or more of the aforementioned copolymer and paramagnetic ion contrast agents, and (ii) scanning the patient using magnetic resonance imaging to obtain visible images of the region.

Further, the present invention encompasses a method for diagnosing the presence of diseased tissue in a patient, the method comprising (i) administering to the patient one or more of the foregoing copolymer and paramagnetic ion contrast agents, and (ii) scanning the patient using magnetic resonance imaging to obtain visible images of any diseased tissue in the region.

The present invention also includes diagnostic kits for magnetic resonance imaging which include one or more of the foregoing contrast agents.

The contrast agents of the present invention are more stable, are less subject to degradation, have better relaxivity, possess higher signal intensity, are more easily targeted for biodistribution, have less toxicity, are less antigenic, and/or are less costly to use than many of the contrast agents known heretofore.

Although not intending to be bound by any particular theory of operation, it is believed that because the specific chelating agent units are an integral part of a copolymer chain which also contains other monomeric units that possess coordinating atoms, the contrast agents of the present invention generally exhibit even higher stability constants for the paramagnetic ions than the single chelating agent units themselves. By controlling the particular monomeric units and the length of the copolymer, biodistribution and specific targetability can also be efficiently and effectively controlled with the subject invention. In view of the very high stability constants of the copolymer for the paramagnetic ions, and because of the ability to prepare the contrast agents with nontoxic and nonantigenic monomeric units, the contrast agents of the invention are safer than many of the contrast agents known heretofore. Also, due to the nondegradability and the ability to disperse the paramagnetic ions along the copolymer chain, the contrast agents of the invention result in surprisingly high relaxivity. The high relaxivity, in turn, serves to decrease the requisite dosage levels. The lower overall concentrations of the contrast agents may thus often be used to achieve the same, or in many cases a better degree of, contrast enhancement results. This has benefits not only in terms of toxicity, by avoiding the use of large amounts of the potentially toxic contrast agents, but also in terms of cost, since less of the contrast agents are used.

These and other aspects and advantages of the subject invention, including the use of the subject compounds as x-ray and ultrasound contrast agents, as nuclear medicine imaging agents, for radiotherapy, to treat heavy metal poisoning and to treat metal deficiencies, will become more apparent from the following detailed description.

DETAILED DESCRIPTION OF INVENTION

In accordance with the present invention, one monomeric unit (a first monomer) comprises a compound of the formula [I]

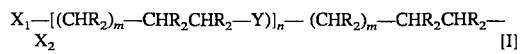

wherein $X_1$ and $X_2$ are, independently, OH, $NH_2$, $NHR_1$, COOH, $COOR_1$, SH, or Z, Y is O, NH, $NR_1$, S, or CO, each Z is, independently, Cl, Br, or I, n is 0–10,000, each m is 0 or 1, each $R_1$ is, independently, a $C_1$–$C_{20}$ substituted or unsubstituted alkyl or cycloalkyl group, and each $R_2$ is, independently, H or OH. By substituted, with regard to $R_1$, it is meant substituted with such moieties as OH, $NH_2$, SH, COOH, $PO_4$, and the like. Preferably, $R_1$ is a polyhydroxy-substituted alkyl or cycloalkyl group. By polyhydroxy-substituted alkyl or cycloalkyl group, it is meant that the alkyl or cycloalkyl group is substituted with at least two hydroxyl groups. Suitable substituted and unsubstituted alkyl or cycloalkyl groups, including polyhydroxy-substituted alkyl or cycloalkyl groups, will be readily apparent to those skilled in the art. Preferable polyhydroxy-substituted alkyl or cycloalkyl groups, for example, include sugar alcohols (such as glycidol, inositol, mannitol, sorbitol, pentaerythritol, galacitol, adonitol, xylitol, and alabitol), monosaccharides (such as sucrose, maltose, cellobiose, and lactose), polysaccharides (such as starch), and synthetic polymers (such as polyvinylalcohol).

In formula [I], preferably n is 0–1000, more preferably n is 0–100, even more preferably n is 1–50, and most preferably n is 1–10. Examples of preferable monomers which fall within the scope of formula [I] are ethylene glycol (EG) (where $X_1$ and $X_2$ are OH, Y is O, n is 0, m is 0, and $R_2$ is H); polyethylene glycol (PEG) (where $X_1$ and $X_2$ are OH, Y is O, n is 1–10,000, m is 0, and $R_2$ is H); 2,2'-ethylenedioxy-diethylamine (EOEA) (where $X_1$ and $X_2$ and $NH_2$, Y is O, n is 2, m is 0, and $R_2$ is H); W,W'-dimercaptopolyethylene glycol (EGS) (where $X_1$ and $X_2$ are SH, Y is O, n is 2, m is 0, and $R_2$ is H); and N,N'-(α,β-dihydroxy-propyl)-2,2'-ethylenedioxy-diethylamine (EOEA-DP) (where $X_1$ and $X_2$ are each $NHR_1$ and $R_1$ is $CH_2CHOHCH_2OH$, Y is O, n is 2, m is 0, and $R_2$ is H). Other suitable first monomers of the formula [I] will be readily apparent to those skilled in the art once armed with the present disclosure, and include, for example, 1,4,7,10-tetraazacyclododecane, 1,3,5-phenylenetriamine, triamino-triethylamine, 1,2-diaminoethane, and N,N'-dimethyl-1,2-diaminoethane, diethylenetriamine, triethylenetetraamine. Other suitable first monomers, which can be employed in lieu of the monomers of formula [I], include 1,3-diaminopropane, 1,4-diaminobutane, 1,5-diamino-3-(2-aminoethyl)-pentane, N,N'-dimethyl-1,2,-diaminopropane, 2-hydroxy-1,3-diaminopropane, 2-amino-1,3-diaminopropane, 2,3-diamino-1,4-butanediol, 1,4-diamino-2,3-butanediol, 1,4-diaminocyclohexane, 1,4-phenylenediamine, 1,1,1-tris(aminomethyl)ethane, 2,2',2"-triaminotriethylamine, tris-(aminomethyl)methane, 1,3,5-triaminocyclohexane, 1,3,5-phenylenetriamine, 2,2-dimethyl1,3-propanediol, tris(2-hydroxyethyl)amine, 1,1,1-tris(hydroxymethyl)ethane, and tris(hydroxymethyl)aminomethane.

Many of the compounds of formula [I] are available commercially. For example, ethylene glycol and polyethylene glycol may be purchased from Aldrich Chemical Co., Milwaukee, Wis., and 2,2'-ethylenedioxy-diethylamine is available from Fluka Inc., in Ronkontoma, N.Y. The formula [I] compounds may also be prepared by conventional techniques such as those polymerization techniques described in McCrum et al., *Principles of Polymer Engineering,* Oxford University Press (New York 1988), the disclosures of each of which are hereby incorporated herein by reference in their entirety.

In accordance with the present invention, a second monomeric unit comprises a compound which is a polynitrilo acid chelating agent having at least two COOH, $COOR_1$, or COZ groups, wherein $R_1$ and Z are as described above. By chelating agent, it is meant an organic compound capable of coordinating with a paramagnetic ion (or other metal). By polynitrilo, it is meant a compound containing at least two nitrogen groups. The COOH groups of the second monomer may, if desired, be in the form of an acid anhydride, as those skilled in the art will recognize, and such variations are intended to be literally encompassed within the term COOH, as employed in connection with the polynitrilo chelating agents. Such polynitrilo chelating agents may include either open chain or cyclic structures, as desired. Polynitrilo chelating agents are well known in the art, and suitable chelating agents will be readily apparent to those skilled in the art, once armed with the present disclosure. Examples of suitable chelating agents include such compounds as ethylenediamine tetraacetic acid (EDTA), diethylenetriamine pentaacetic acid (DTPA), 1,5-di-β-methoxyethylene-iminocarbonyl-methylene- 1,3,5-tricarboxymethylene-1,3,5-triazapentane, 1,5-di-α,β-dihydroxypropeneimino-carbonylmethylene- 1,3,5-tricarboxymethylene-1,3,5-triazapentane, 1,4,7,10-tetraazacyclododecane-1,4,7,10-tetraacetic acid, 1,5,8,12-tetraazacyclotetradecane-1,5,8,12-tetraacetic acid 1,4,7,10-tetraazacyclododecane-N,N',N', N'''-tetraacetic acid (DOTA), 1,4,7,10-tetraazacyclododecane-N,N',N''-triacetic acid (DO3A), 3,6,9-triaza-12-oxa- 3,6,9-tricarboxymethylene-10-carboxy-13-phenyl-tridecanoic acid (B-19036), hydroxybenzyl-ethylenediamine diacetic acid (HBED), N,N'-bis(pyridoxyl-5-phosphate)ethylene diamine-N,N'-diacetate (DPDP), 1,4,7-triazacyclononane-N,N',N''-triacetic acid (NOTA), 1-oxa-4,7,10-triazacyclododecanetriacetic acid (OTTA), 1,4,8,11-tetraazacyclotetradecane-N,N'N'',N'''-tetraacetic acid (TETA), 1,4,8,11-tetraazacyclodecanetetraacetic acid, triethylenetetraamine hexaacetic acid (TTHA), 1,2-diaminocyclohexane-N,N,N',N'-tetraacetic acid, and triethylenetetraaminehexaacetic acid, as well as anhydrides of the foregoing, such as, for example, ethylene diamine tetraacetic acid dianhydride (EDTA-anhydride), and diethylenetriamine pentaacetic acid dianhydride (DTPA-anhydride). More preferably, the complexing agents are DTPA, EDTA and DOTA, most preferably DTPA and EDTA. Examples of these and other chelating agents are described in Gibby, U.S. Pat. No. 4,933,441 and PCT/EP90/01792 (Publication No. WO 91/05762), the disclosures of each of which are hereby incorporated herein by reference in their entirety.

A number of the foregoing chelating agents are available commercially, such as, for example, ethylenediamine tetraacetic acid (and its anhydride), diethylenetriamine pentaacetic acid (and its anhydride), and diethylenetriamine pentaacetic acid (and its anhydride), which may be purchased from Aldrich Chemical Co., Milwaukee, Wis., or Sigma Chemical Co., St. Louis, Mo. Such chelating agents may also be prepared by conventional techniques, as will be readily apparent to those skilled in the art.

In accordance with the present invention, a third monomeric unit may comprise a targeting agent, the targeting agent having an OH, $NH_2$, $NHR_1$, COOH, $COOR_1$, SH, or COZ group, wherein $R_1$ and Z are as described above. The purpose of the targeting agent is to assist in selectively directing the agent to a particular region of the body. Targeting agents are well known and understood in the diagnostic and therapeutic areas, and suitable agents will be readily apparent to those skilled in the art, once armed with the present disclosure. Suitable targeting agent include antibodies (such as monoclonal antibodies, either whole or in part), glycoproteins, and saccharides. Exemplary monoclonal antibodies include the Fab'2 fragments of anticarcinoembryonic antigen monoclonal antibody (for targeting metastatic colon carcinoma) and anti-leukocyte antigen monoclonal antibody (for targeting white blood cells). A suitable saccharide includes cellobiose (for targeting the liver).

The copolymer may be prepared by polymerizing the first and second monomer types, and if desired, the third monomer type, using polycondensation polymerization techniques. Such polymerization techniques include those described in McCrum et al., *Principles of Polymer Engineering*, Oxford University Press (New York 1988), the disclosures of each of which are hereby incorporated herein by reference in their entirety. Specifically in accordance with the polymerization process, the first, second, and third (if desired) monomers bind to one another to form a copolymer through an ester, amide, or carboxylic thioester linkage of at least one of the reactive functional groups OH, $NH_2$, $NHR_1$, COOH, $COOR_1$, SH, or Z groups of the first monomer, at least one of the reactive functional COOH, $COOR_1$, or COZ groups of the second monomer, and at least one of the reactive functional OH, $NH_2$, $NHR_1$, COOH, $COOR_1$, SH, or COZ groups of the third monomer, to the extent a third monomer is present. If desired, one may employ any one of a number of condensation reagents such as dicyclohexyl carboimide (DCC), to facilitate the polymerization reaction. Alternatively, if desired, the polynitrilo chelating agent (the second monomer type) may be employed in the form of an acid anhydride, to facilitate the polymerization reaction.

As those skilled in the art will recognize, the copolymer may take any one of a variety of forms such as linear, branched, acyclic and/or cross-linked, depending upon the particular monomers employed, the number of reactive sites that the monomers possess, the particular reaction conditions, etc., as will be readily apparent to those skilled in the art, once armed with the present disclosure, so long as the copolymer comprises at least two of the first monomer and at least one of the second monomer, linked as described above. The copolymer may also contain, if desired, at least one of the third monomer. The copolymer may consist of more than one type of first monomer, more than one type of second monomer, and more than one type of third monomer. Preferably, the copolymer is a linear or branched copolymer, most preferably a linear copolymer. Also, preferably the copolymer is comprised of only first and second monomeric units, and preferably the first and second monomeric units are present as alternate units in the copolymer chain (that is, a first monomer is attached to a second monomer, which is attached to a first monomer, and so on), or in a 2:1 ratio (that is, two of a first monomer attached to one of a second monomer, which is attached to two of a first monomer, which is attached to one of a second monomer, and so on). Preferably, the copolymer comprises at least three of the first monomer and at least two of the third monomer.

Preferred copolymers of the invention include N,N'-bis-polyethyleneglycol-carbonylmethylene-ethylenediamine-N, N'-diacetate, poly-N,N'-di- 2,2'-(ethylenedioxy)diethylene-iminocarbonylmethylene-ethylenediamine-N,N'-diacetate, poly-1,5-di-(2,2'-ethylenedioxy-diethyleneiminocarbonyl-methylene)- 1,3,5'-triazapentane- 1,3,5-triacetate, poly-N, N'-di-polyethyleneglycol-W,W' -diethylenethiocarbonylm-ethylene-ethylenediamine-N,N'-diacetate, poly-1,5-di-polyethyleneglycol-W,W'-diethylenethiocarbonylmethylene- 1,3,5-triazaheptane-1,3, 5-triacetate, and poly-N,N'-bis- 2,2'-ethylenedioxy-diethylene-amino-N-(α,β -dihydroxypropane)-carbonylmethylene-ethylenediamine-N,N'-diacetate.

As those skilled in the art will recognize in view of the present disclosure, the molecular weight of the copolymer can vary widely, as desired. Preferably, however, the molecular weight of the copolymer is between about 1,000 and about 500,000 (weight average molecular weight), most preferably between about 3,000 and about 30,000. As those skilled in the art will recognize, the molecular weight of the particular copolymer employed depends, in part, on the particular use for which it is intended. For example, copolymers of molecular weight of about 60,000 to about 100,000 are particularly useful as perfusion agents to assess the vascularity of tissues and to enhance the signal from blood on magnetic resonance angiography. Because of their molecular weight, copolymers of molecular weight of about 60,000 to about 100,000 are retained within the blood vessels rather than equilibrate with the interstitial fluids. Copolymers in the range of about 10,000 to about 50,000, because of their small size, are especially useful as contrast agents for assessing the size of fenestrae or capillary pores. By being able to control the size of the copolymers, the biodistribution of the copolymeric contrast agents can be controlled via molecular weight. For reasons of increased diagnostic effectiveness, it is generally preferable that the first and second monomers of the copolymer (and the third monomers, where third monomers are included) comprise, collectively, at least about 10 monomers, more preferably at least about 20 monomers, even more preferably at least about 50 monomers, still more preferably at least about 100 monomers, and most preferably at least about 150 monomers, and may include preferably up to about 400, more preferably up to about 350, even more preferably up to about 300, still more preferably up to about 250 monomers, and most preferably up to about 200 monomers, although the number of monomers, may if desired, range up to about 500, 1000, 2000, etc.

As noted above, the present invention is directed, inter alia, to copolymers comprised of specific monomeric units in association with paramagnetic ions.

Thus in accordance with one aspect of the invention particularly suited to magnetic resonance imaging, the contrast agent further comprises a paramagnetic ion coordinated to the chelating agent. Exemplary paramagnetic contrast agents suitable for use in the subject invention include transition, lanthanide (rare earth) and actinide elements, as will be readily apparent to those skilled in the art, in view of the present disclosure. Preferable elements include Gd(III), Mn(II), Cu(II), Cr(III), Fe(II), Fe(III), Co(II), Er(II), Ni(II), Eu(III), Dy(III), Yb(III), and Ho(III). More preferably, the elements include Gd(III), Mn(II) and Fe(III), especially Gd(III). If desired, different paramagnetic ions may be employed in combination with one another and may be chelated to a combination of different chelating agent types within the copolymer chain. In magnetic resonance angiography, for example, both paramagnetic shift reagents (e.g., Dy(III)) and paramagnetic relaxation agents (e.g., Gd(III)) may be employed in conjunction with one another.

Preferred copolymer and paramagnetic ion combinations include N,N'-Bis-polyethyleneglycol-carbonylmethylene-ethylenediamine-N,N'-diacetate in combination with Mn(II), poly-N,N'-di- 2,2'-(ethylenedioxy)diethyleneiminocarbonyl-methylene-ethylenediamine-N,N'-diacetate in combination with Mn(II), poly-1,5-di-( 2,2'-ethylenedioxy-diethyleneiminocarbonyl-methylene)- 1,3,5-triazapentane-1,3,5-triacetate in combination with Gd(III), poly-1,5-di-( 2,2'-ethylenedioxy-diethyleneiminocarbonylmethylene)- 1,3,5-triazapentane- 1,3,5-triacetate in combination with Fe(III), poly-N,N' -di-polyethyleneglycol-W,W' -diethylenethiocarbonyl-methylene-ethylenediamine-N,N'-diacetate in combination with Mn(II), poly-1,5-di-polyethyleneglycol-W,W'-diethylenethiocarbonylmethylene- 1,3,5-triazaheptane-1,3,5-triacetate in combination with Gd(III), poly-1,5-di-polyethyleneglycol-W,W'-diethylenethiocarbonylmethylene 1,3,5-triazaheptane-1,3,5-triacetate in combination with Fe(III), and poly-N,N'-bis-2,2 '-ethylenedioxydiethyleneamino-N-($\alpha,\beta$ -dihydroxy-propane)-carbonylmethylene-ethylene-diamine-N,N'-diacetate in combination with Mn(II).

The present invention is useful in imaging a patient generally, and/or in specifically diagnosing the presence of diseased tissue in a patient. The imaging process of the present invention may be carried out by administering a copolymer with a chelated paramagnetic ion (a contrast agent of the invention) to a patient, and then scanning the patient using magnetic resonance imaging to obtain visible images of an internal region of a patient and/or of any diseased tissue in that region. By region of a patient, it is meant the whole patient or a particular area or portion of the patient. The contrast agents of the invention are particularly useful in providing images of the gastrointestinal region of a patient and/or of any diseased tissue in that region, but can also be employed more broadly such as in imaging the vasculature, the liver, kidney, bladder, and heart, as well as other regions of the body. The phrase gastrointestinal region or gastrointestinal tract, as used herein, includes the region of a patient defined by the esophagus, stomach, small and large intestines, and rectum. The phrase vasculature, as used herein, denotes the blood vessels in the body or in an organ or part of the body. The patient can be any type of mammal, but most preferably is a human. The copolymer and paramagnetic ion combination of the present invention is also particularly useful in vascular imaging applications using magnetic resonance. As shown in Table III, for example, following intravenous injection of Poly-EDTA-EOEA-DP-Mn, there is appreciable contrast enhancement. These studies have also shown increased signal intensity in the blood over single chelating agent and paramagnetic ion units.

As one skilled in the art would recognize, administration may be carried out in various fashions, such as intravascularly, orally, rectally, etc., using a variety of dosage forms. The useful dosage to be administered and the particular mode of administration will vary depending upon the age, weight and the particular mammal and region to be scanned. Typically, dosage is initiated at lower levels and increased until the desired contrast enhancement is achieved. By way of general guidance, typically between about 0.1 mg and about 1 g of copolymer, and between about 1 and about 50 micromoles of paramagnetic ion, per kilogram of patient body weight, is administered, although higher and lower amounts can be employed. Various combinations of copolymers and paramagnetic ions may be used to modify the relaxation behavior of the contrast agent. In carrying out the method of the present invention, the contrast medium can be used alone, or in combination with other diagnostic, therapeutic or other agents. Such other agents include excipients such as flavoring or coloring materials.

Kits useful for magnetic resonance imaging comprising the contrast agents of the invention in addition to conventional proton magnetic resonance imaging kit components are also within the ambit of the present invention. Such conventional proton magnetic resonance imaging kit components may vary depending upon the particular application, but include such components as anti-oxidants to prevent oxidation in storage (a variety of applications), anti-gas agents (primarily gastrointestinal applications), T2 relaxation agents (primarily gastrointestinal applications), osmolality raising agents (a variety of applications), viscosity and bulking agents (primarily gastrointestinal applications), and buffering agents (a variety of applications), as well as other components which will be readily apparent to those skilled in the art, once armed with the present disclosure, such as those described in Weinmann et al., U.S. Pat. No. 4,719,098, and The United States Pharmacopeia—The National Formulary, United States Pharmacopeial Convention, Inc., USP XXII NFXVII, Mack Printing Co., Easton, Pa. (1989), the disclosures of each of which are hereby incorporated herein by reference in their entirety.

Anti-oxidants, while not necessary due to the excellent stability of the copolymers of the invention, may, if desired, be employed in a final product formulation. Suitable anti-oxidants include vitamin C (ascorbic acid), vitamin E (tocopherol), and retinoic acid. Other suitable anti-oxidants will be readily apparent to those skilled in the art. The anti-oxidants may be employed in certain applications to keep paramagnetic ions, such as manganese, in their more paramagnetically effective reduced state, that is, for example, in the Mn(II) state, rather than the Mn(III) state. Suitable concentrations of antioxidants will be readily apparent to those skilled in the art.

For use as gastrointestinal contrast agents, the kit may also include anti-gas agents, that is, compounds that serve to minimize or decrease gas formation, dispersion and/or adsorption. Such antigas agents include antacids, antiflatulents, antifoaming agents, and surfactants such as activated charcoal, aluminum carbonate, as well as other agents well known in the art. The concentration of such anti-gas agents may vary widely, as desired, as will be readily apparent to those skilled in the art. Typically, however, such agents are employed in concentrations of between about 20 and about 2000 ppm, most preferably in concentrations between about 50 and about 1000 ppm.

For gastrointestinal applications, the kit may include T2 relaxation agents such as bismuth, barium, kaolin, atapulgite, ferric oxide. These may be employed in concentrations between about 1% and about 10% by weight, although higher or lower concentrations may be allowed.

Osmolality raising agents are useful to adjust the osmolality of the product, and may be included as kit components. For example, for vascular administration, osmolality raising agents may be employed to achieve iso-osmolality. For gastrointestinal administration, such agents may be employed to achieve iso-osmolality or hypo-osmolality. Suitable osmolality agents include polyols and sugars, for example, mannitol, sorbitol, arabitol, xylitol, glucose, sucrose, fructose, and saccharine, with mannitol and sorbitol being most preferred. The concentration of such osmolality raising agents may vary, as desired, however, generally a range of about 5 to about 70 g/l, preferably about 30 to about 50 g/l of the contrast medium. Such compounds may also serve as sweeteners for the ultimate formulation, if desired.

Viscosity and bulking agents include various synthetic and natural polymers, as well as other agents which are well known in the art to provide viscosity and/or bulking. Particularly useful are xanthan gum, pectin, and the like. Such compounds may be employed in varying amounts, as those skilled in the art would recognize, but preferably are employed in amounts of about 2 to about 40 g/l, preferably about 10 to about 30 g/l of the contrast medium.

Buffering agents, that is buffers, buffer mixtures, and bases, may be utilized to stabilize the copolymer and paramagnetic ion complex. Such buffering agents are well known in the art, and suitable buffering agents will be readily apparent to those skilled in the art. If employed, the buffering agents may be used in varying amounts, as will be readily apparent to the skilled artisan, generally in concentrations between about 5 and about 40 mmol/l.

The magnetic resonance imaging techniques which are employed are conventional and are described, for example, in D. M. Kean and M. A. Smith, *Magnetic Resonance Imaging: Principles and Applications*, (William and Wilkins, Baltimore 1986). Contemplated MRI techniques include, but are not limited to, nuclear magnetic resonance (NMR) and electronic spin resonance (ESR). The preferred imaging modality is NMR.

The copolymeric magnetic resonance contrast agents can be used to bind shift reagents (e.g., Dy(III)), or relaxation agents (e.g., Gd(III)), as well as mixtures thereof (e.g., Dy(III) with Gd(III)), and thus have applications in magnetic resonance spectroscopy. For example, a copolymer binding both Dy(III) and Gd(III) will be useful in sodium spectroscopy, serving to both shift and to narrow the signal from the sodium peak. As one skilled in the art would recognize, there will be numerous applications of the copolymeric contrast agents for magnetic resonance spectroscopy.

The contrast agents of the present invention have been shown to be extremely useful as contrast enhancement agents in magnetic resonance imaging. The subject contrast agents are more stable, are less subject to degradation, have better relaxivity, possess higher signal intensity, are more easily targeted for biodistribution, have less toxicity, are less antigenic, and/or are less costly to use than many of the contrast agents known heretofore. Although not intending to be bound by any particular theory of operation, it is believed that because the specific chelating agents are an integral part of a copolymer chain which also contains other monomeric units that possess ligands, the contrast agents of the present invention generally exhibit even higher stability constants for the paramagnetic ions than the chelating agents themselves. By controlling the particular monomeric units and the length of the copolymer, biodistribution and specific targetability can also be efficiently and effectively controlled with the subject invention. In view of the very high stability constants of the copolymer for the paramagnetic ions, and because of the ability to prepare the contrast agents with nontoxic and nonantigenic monomeric units, the contrast agents of the invention are safer than many of the contrast agents known heretofore. Also, due to the nondegradability and the ability to disperse the paramagnetic ions along the copolymer chain, the contrast agents of the invention result in surprisingly high relaxivity. The high relaxivity, in turn, serves to decrease the requisite dosage levels. The lower overall concentrations of the contrast agents may thus often be used to achieve the same, or in many cases a better degree of, contrast enhancement results. This has benefits not only in terms of toxicity, by avoiding the use of large amounts of the potentially toxic contrast agents, but also in terms of cost, since less of the contrast agents are used. These and other advantages described herein of the present invention will be readily apparent to those skilled in the art, upon reading the present disclosure.

The novel copolymeric compounds are also useful as X-ray and ultrasound contrast agents, for nuclear medicine as imaging agents, and for radiotherapy, with administration being carried out as described above. For X-ray and ultrasound, the copolymers may be employed to chelate heavy metals such as Hf, La, Yb, Dy, Gd and Pb. For nuclear medicine, the copolymer may be employed to chelate radioactive metals, in particular Tc, Cu, In, Sm, Ru and Y. For use as local radiation sensitizers for radiation therapy, the copolymers may chelate radioactive metals such as those described above, and optionally a variety of heavy metals and lanthanide (rare earth) metals as described above. In this regard, the selection of heavy metals and rare earths may be done to match the energy absorption spectrum of the incident radiation and increase conversion of Auger electrons, high energy particles and emission of secondary radiation.

Additionally, the copolymers of the invention may be used to treat heavy metal poisoning, e.g., for iron, arsenic or lead poisoning. For treatment of heavy metal poisoning, the copolymers will generally be administered alone without chelated ions, although as one skilled in the art will recognize, in some applications of metal poisoning treatment, some calcium or other metal ions may be added to the copolymer formulation prior to administration. Otherwise, administration may be carried out as described above. The copolymers may be used to treat poisoning from such metal ions as Mg, Ca, Sc, Ti, V, Cr, Mn, Mg, Fe, Eu, Er, Pb, Co, Ni, Cu, Zn, Ga, St, Y, Zr, Tc, Ru, In, Hf, W, Re, Os, Pb, Bi, Dy, Mn, Gd, Hf, La, Yb, Tc, In and As.

Additionally, the subject copolymers may be chelated to a metal and used as therapeutic agents to treat metal deficiencies, with administration being carried out as described above. The copolymers are particularly useful in this regard as their molecular size can be varied, and thus they may be targeted in vivo. By preparing copolymers of a relatively large size, e.g., greater than about 60,000 molecular weight, renal clearance is greatly slowed and plasma circulation time is increased. The copolymers can then be used to provide a slowly exchangeable pool of the deficient metal ion in vivo. Metal ions which may be bound to the copolymers for treatment of deficiency include Mn, Fe, Zn, Co, Ni, Cu, Cr, Mg, Se and Ca.

The present invention is further described in the following examples. In all of the examples, as well as throughout the present specification, all molecular weights are weight average molecular weights. These examples are not to be construed as limiting the scope of the appended claims.

EXAMPLES

Example 1
Synthesis of Manganese N,N'-Bis-polyethyleneglycol-carbonylmethylene-ethylene-diamine N,N'-diacetate (PEG-EDTA-PEG-Mn)

Structure

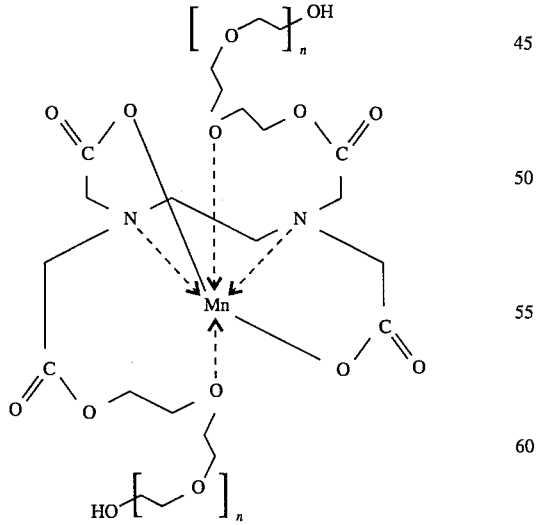

Ethylenediamine-N,N,N',N'-tetraacetic acid (0.5 g) and 1.76 g polyethyleneglycol (MW 400) were dissolved in 10 ml dimethylformamide (DMF). Dimethylaminopyridine (30 mg) was added as catalyst. The mixture was cooled to between about 0° C. and about 5° C. A solution of 0.91 g dicyclohexylcarboimide in 10 ml of DMF was added dropwise into the mixture, with continual stirring. Stirring was continued while maintaining the temperature between about 0° C. and about 50° C. for four hours, at which time the temperature of the mixture was raised to room temperature, and stirring was continued over night. The temperature was then maintained between about 45° C. and about 50° C., and stirred for an additional seven hours. The DMF was evaporated under reduced pressure to a small volume and diluted with 15 ml water. Dicyclohexyl urea was precipitated as a white solid and isolated by filtration. The water was evaporated and 2 g of viscous liquid PEG-EDTA-PEG was obtained.

PEG-EDTA-PEG (2 g) was dissolved in 50 ml of water. Manganese carbonate (0.25 g) was suspended in the mixture and stirred at about 40° C. for eight hours. The undissolved precipitate was filtered off and the filtrate evaporated to dryness to produce a viscous liquid-like manganese containing copolymer, Mn-PEG-EDTA-PEG (2 g), having a molecular weight of about 1,000.

Example 2
Synthesis of Manganese Poly-N,N'-di-2,2'-(ethylenedioxy) diethyleneiminocarbonylmethylene-ethylenediamine-N, N'-diacetate (Poly-EDTA-EOEA-Mn)

Structure

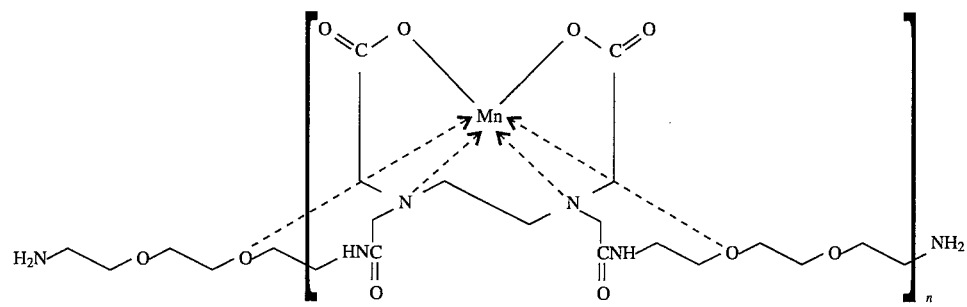

EDTA anhydride (5.12 g) and 2,2'-ethylenedioxydiethylamine 2.96 g were dissolved in 200 ml anhydrous methanol and stirred for twenty four hours at room temperature. The reaction temperature was raised to about 40° C., and then stirred for an additional seven hours. Two layers resulted. The upper layer was removed by decanting. The bottom layer was a very viscous liquid, and was evaporated to dryness. The copolymer Poly-EDTA-EOEA (5.1 g) was obtained.

Copolymer Poly-EDTA-EOEA (4 g) was dissolved in 50 ml of water. Manganese carbonate (1.15 g) was suspended in the reaction mixture and stirred at room temperature for twenty four hours. Most of manganese carbonate was dissolved in the mixture. The reaction temperature was then raised to about 50° C. and stirred for an additional six hours. The small amount of undissolved precipitate was filtered out and the solution was evaporated to dryness, to produce a solid manganese containing copolymer Poly-EDTA-EOEA-Mn (4.2 g), having a molecular weight of about 30,000 to 50,000.

Example 3
Synthesis of Gadolinium Poly-1,5-di-(2,2'-ethylenedioxydiethyleneiminocarbonylmethylene)-1,3,5-triazapentane-1,3,5-triacetate (Poly-DTPA-EOEA-Gd)

DTPA anhydride (3.57 g) and 2,2'-ethylenedioxydiethylamine (1.48 g) were dissolved in 100 ml anhydrous methanol and stirred for twenty-four hours at room temperature. The temperature was then raised to about 45° C. and stirred for an additional four hours. The reaction solution was evaporated to dryness producing 5 g solid copolymer (Poly-DTPA-EOEA).

Poly-DTPA-EOEA (2 g) was dissolved in 50 ml water. Gadolinium oxide (0.72 g) was suspended in the reaction mixture and stirred at a temperature between about 80° C. and about 90° C. for 16 hour. A small amount of undissolved precipitate was then filtered off, the solution evaporated, producing a yellow-white glass like solid gadolinium containing copolymer (Poly-DTPA-EOEA-Gd) (2.3 g), having a molecular weight of about 30,000 to 50,000.

Example 4
Synthesis of Ferric Poly-1,5-di-( 2,2'-ethylenedioxydiethyleneimineocarbonylmethylene)- 1,3,5-triazapentane-1,3,5-triacetate (Poly-DTPA-EOEA-Fe)

Structure

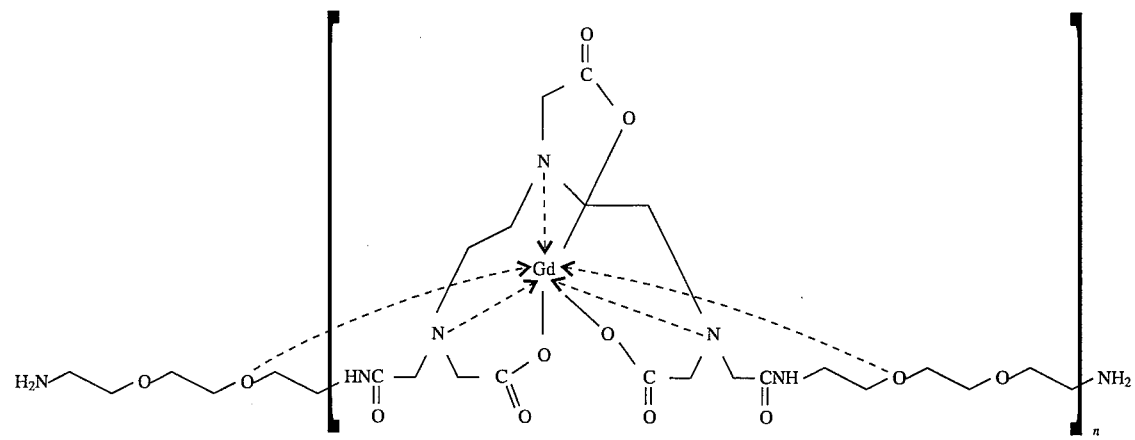

Structure

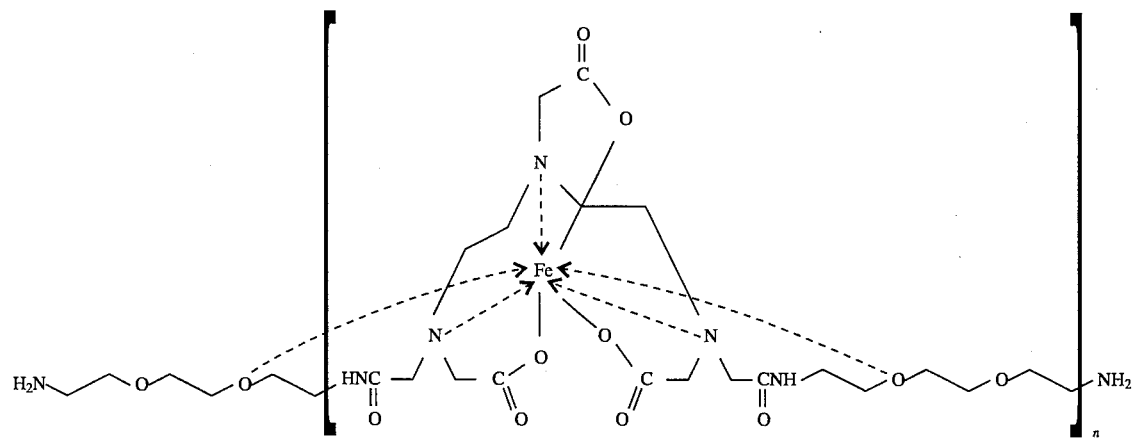

Poly-DTPA-EOEA (2 g), prepared substantially as set forth in Example 3, was dissolved in 50 ml of water. A solution of 1 g ferric chloride in 50 ml water ($FeCl_3$, $6H_2O$) was added dropwise to the Poly-DTPA-EOEA solution, with stirring. The solution was then stirred at room temperature for 2 hours. A small amount of precipitate was filtered off, and the solution was evaporated to dryness. The resulting solid was dissolved in ethanol, evaporated, and dried again. The evaporation and drying step was repeated two additional times, resulting in a yellow-white glass like solid iron containing copolymer Poly-DTPA-EOEA-Fe (2.4 g), having a molecular weight of about 30,000 to 50,000.

Example 5
Synthesis of Manganese Poly-N,N' -di-polyethyleneglycol-w,w'-diethylenethiocarbonylmethylene-ethylenediamine-N,N' -diacetate (Poly-EDTA-EGS-Mn)

chloric acid. The ethanol was evaporated off. The residues were extracted from the solution with chloroform, the chloroform was evaporated from the solution, resulting in a viscous liquid, w,w'-dimercapto-polyethyleneglycol.

EDTA anhydride (2.56 g) and w,w'-dimercaptopolyethyleneglycol (4.42 g) were dissolved in anhydrous diethyleneglycol dimethyl ether and refluxed for eight hours. The solvent was evaporated off, resulting in the copolymer Poly-EDTA-EGS.

Poly-EDTA-EGS (3.49 g) and manganese carbonate (0.58 g) were mixed with 100 ml water and then stirred over night. The water was evaporated off, resulting in the manganese containing copolymer Poly-EDTA-EGS-Mn, having a molecular weight of about 30,000 to 50,000.

Structure

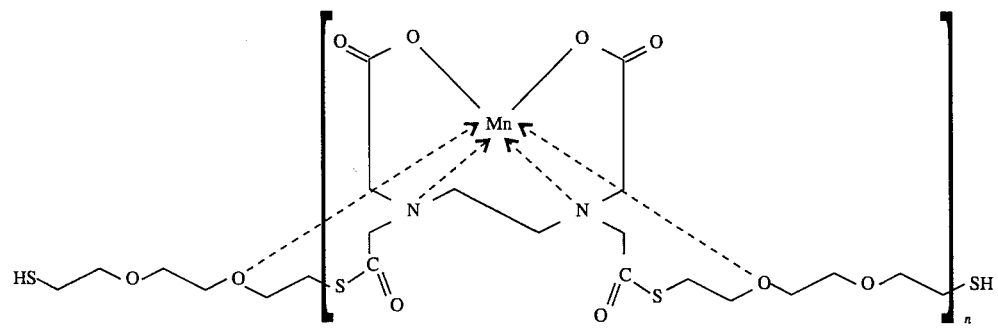

First, w,w'-dimercapto-polyethyleneglycol was synthesized as follows. Thiourea (1.52 g) and w,w,'-dibromopolyethyleneglycol (MW 540) (5.4 g) were dissolved in ethanol, refluxed for eight hours, then acidified with a dilute hydro- Example 6
Synthesis of Gadolinium (or Ferric) Poly- 1,5-di-polyethyleneglycol-w,w'-diethylenethiocarbonylmethylene- 1,3,5-triazaheptane-1,3,5-triacetate (Poly-EDTA-EGS-Gd or Poly-EDTA-EGS-Fe)

Structure

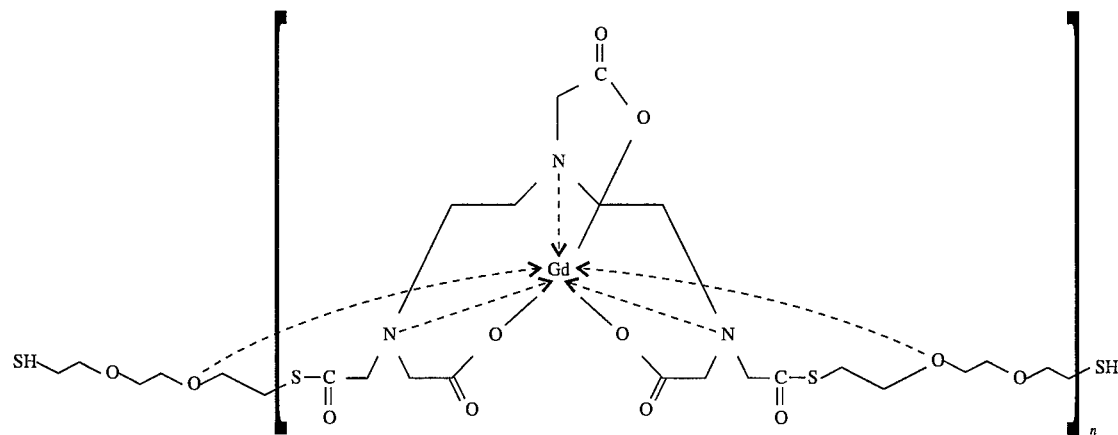

DTPA anhydride (8.57 g) and w,w'-dimercaptopolyethyleneglycol (4.42 g) were dissolved in anhydrous diethyleneglycol dimethyl ether and refluxed for eight hours. The solvent was evaporated off, producing the copolymer Poly-DTPA-EGS.

Structure

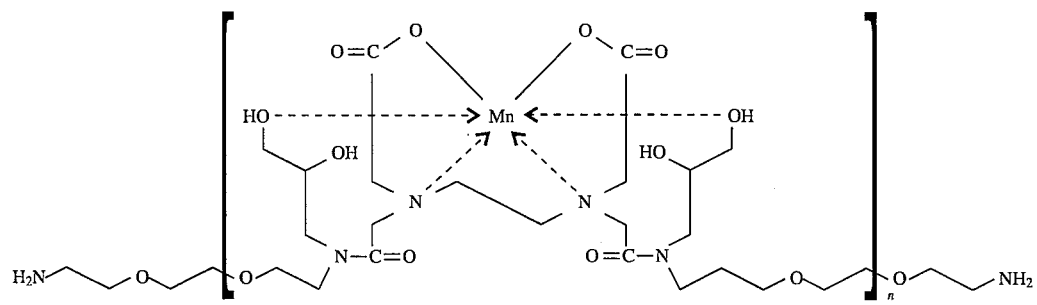

Poly-DTPA-EGS (4 g) and gadolinium chloride (1.31 g) (or Ferric chloride (1.31 g)) was mixed with 100 ml water and the solution evaporated to dryness. Ethanol (50 ml) was added to redissolve the polymer, and the solution was again evaporated to dryness to remove residual hydrogen chloride resulting from the addition of gadolinium (or ferric) chloride. The redissolving and drying step was repeated several times, resulting in the copolymer Poly-DTPA-EGS-Gd (or Poly-DTPA-EGS-Fe), having a molecular weight of about 30,000 to 50,000.

Example 7

Synthesis of Manganese Poly-N,N'-bis- 2,2'-ethylenedioxydiethylenenitrilo-N-($\alpha,\beta$ -dihydroxy-propane)-carbonylmethylene-ethylenediamine-N,N'-diacetate N,N'-($\alpha,\beta$-dihydroxy-propyl)-2,2'-ethylenedioxy-di ethylamine (EOEA-DP) was prepared as follows. In dried methanol (50 ml) was dissolved 2,2'-(ethylenedioxy)diethylamine (8.88 g), and the solution was heated to 60° C. Glycidol (8.88 g) was added dropwise, with stirring. The reaction mixture was kept under reflux and glycidol was added in 2 hours, then stirred for one additional hour. The methanol was evaporated off, resulting in 8.5 g .of EOEA-DP, as a viscous liquid.

Poly-N,N'-bis- 2,2'-ethylenedioxydiethylenenitrilo-N-($\alpha,\beta$ -dihydroxy-propane)-carbonylmethylene-ethylenediamine-N, N'-diacetic acid (EDTA-EOEA-DP) was then prepared as follows. EOEA-DP (1.48 g) was mixed with EDTA anhydride (1.28 g) in 50 ml dried methanol and stirred overnight. The methanol was then evaporated forming a white solid copolymer EDTA-EOEA-DP (2.7 g).

EDTA-EOEA-DP (1.35 g) was next dissolved in water (50 ml) and mixed with manganese carbonate (0.3 g). The solution was stirred overnight, resulting in a transparent reaction mixture. The solution was evaporated to dryness, resulting in a solid copolymer Mn-EDTA-EOEA-DP (1.4 g), having a molecular weight of about 30,000 to 50,000.

Example 8

$T_1$ and $T_2$ relaxivity of the copolymers Poly-EDTA-EOEA-Mn and Poly-EDTA-EOEA-DP-Mn was measured using a Toshiba MRT-50A scanner operating at 0.5 Tesla. Serial concentrations of the various polymers were prepared in a phantom and scanned by MRI. To measure $T_1$, TE was held constant at 15 milliseconds and TR's of 100, 300, 450, 600, 900, 1200, 1800, 2500 and 3500 milliseconds were run. For $T_2$ measurement, TR was held constant at 3500 milliseconds and TE's of 30 through 250 milliseconds were run. The signal intensities were measured by selecting a region of interest from the CRT monitor, and to determine $T_1$ and $T_2$ relaxation values a least squares fit was performed on the different data sets. The $T_1$ and $T_2$ measurements are shown in Table I below.

TABLE I

RELAXIVITY OF MANGANESE BLOCK COPOLYMERS

| Sample | 1/T1 $mmol^{-1}$ $sec^{-1}$ | 1/T2 $mmol^{-1}$ $sec^{-1}$ |
|---|---|---|
| $MnCl_2$ | 7.57 ± 0.42 | 24.5 ± 3.79 |
| Gd-DTPA | 4.69 ± 0.279 | 5.17 ± 0.148 |
| Mn-EDTA-MEA | 3.12 ± 0.124 | 5.61 ± 1.0108 |
| POLY-EDTA-EOEA-Mn | 6.07 ± 0.307 | 11.35 ± 0.0212 |
| POLY-EDTA-EOEA-DP-Mn | 7.41 ± 0.526 | 8.93 ± 0.322 |

In Table I, $MnCl_2$ (free manganese ion in solution), Gd-DTPA, and the complex Mn-EDTA-MEA are included for reference. Free manganese ion is a good, albeit toxic, relaxation agent with particularly strong T2 relaxivity, but is much less effective after chelation as shown by Mn-EDTA-MEA and Gd-DTPA. Gd-DTPA is somewhat more effective than Mn-EDTA-MEA, but the manganese copolymers are much more effective than Gd-DTPA and Mn-EDTA-MEA.

Poly-EDTA-EOEA-DP-Mn displays an 18.1% improvement in T1 relaxivity over POLY-EDTA-EOEA-Mn, however, POLY-EDTA-EOEA-DP-Mn has an opposite effect on T2 relaxivity, decreasing the rate. There is a 10% difference between the two samples for T2.

Example 9

Stability of Poly-EDTA-EOEA-Mn in serum was determined by incubating the copolymeric manganese complex in phosphate buffered saline (PBS), 10% serum, and 50% serum at about 35° C. for 12, 24 and 48 hours, as shown in Table IIA, below.

TABLE IIA

INITIAL SOLUTIONS FOR SERUM STABILITY TEST OF POLY-EDTA-EOEA-Mn

| Solution | Mn-POLY-EDTA-EOEA |
|---|---|
| PBS | 0.1151 |
| 10% serum (by volume) | 0.1043 |
| 50% serum (by volume) | 0.1052 |

Ten ml of each solution were withheld to establish baseline Mn concentration. The remaining 40 ml solutions were each placed in Spectra/pol CE MWCO 100 dialysis membranes and suspended in 500 ml phosphate buffered saline in a shaking water bath at 35° C. Further samples were taken at 12, 24 and 48 hours. After each sample was taken, the phosphate buffered saline was replaced with fresh. The concentrations of manganese were determined before and after incubation using a spectrophotometric method. The results are shown below in Tables IIB and IIC. The low level of change in each sample indicates a very high serum stability for the manganese copolymer.

TABLE IIB

SERUM STABILITY OF POLY-EDTA-EOEA-Mn

| | Manganese in Milligrams | | | | |
|---|---|---|---|---|---|
| | Init. | 12 hr* | 24 hr | 48 hr | Total change |
| PBS | 10.87 | 9.04 | 10.40 | 10.17 | 0.70 |
| 10% serum | 10.75 | 8.43 | 9.71 | 9.79 | 0.96 |
| 50% serum | 9.56 | 7.71 | 8.84 | 8.84 | 0.72 |

TABLE IIB

SERUM STABILITY OF POLY-EDTA-EOEA-Mn

| | Percentage of Manganese | | | | |
|---|---|---|---|---|---|
| | Init. | 12 hr* | 24 hr | 48 hr | Total change |
| PBS | 100% | 83.16% | 95.68% | 93.56% | 6.44% |
| 10% serum | 100% | 78.42% | 90.33% | 91.07% | 8.93% |
| 50% serum | 100% | 80.65% | 92.47% | 92.47% | 7.53% |

*These values are low because of some loss of sample during preparation.

Example 10

Two rats were injected intravenously with doses of 25 and 50 micromoles per kg of poly-EDTA-EOEA-DP-Mn (a dose between one-quarter and one-half that presently employed for the contrast agent Gd-DTPA), and T1 weighted spin echo images were obtained both before and after intravenous injection of contrast. The results are shown in Table III below.

TABLE III

Poly-EDTA-EOEA-DP-Mn COPOLYMERS IN VIVO ENHANCEMENT

| | Rat A | Rat B |
|---|---|---|
| | Dose | |
| | 25 µmole/kg Signal Intensity | 50 µmole/kg Signal Intensity |
| Pre Contrast | | |
| Liver | 468 ± 15 | 415 ± 20 |
| Tumor | 385 ± 60 | 377 ± 20 |
| Heart | 137 ± 29 | 114 ± 20 |
| Kidney | 383 ± 37 | 448 ± 68 |
| Contrast-to-Noise (liver/tumor) | 11.9 | 5.4 |
| Post Contrast | | |
| Liver | 922 ± 45 | 850 ± 43 |
| Tumor | 559 ± 40 | 485 ± 68 |
| Heart | 407 ± 30 | 303 ± 12 |
| Kidney | 996 ± 82 | 958 ± 76 |
| Contrast-to-Noise (liver/tumor) | 51.9 | 52.1 |

Peak contrast was obtained at the dose of 25 micromoles per kg. Noise remained constant at 12.0±7 signal intensity units. Liver/tumor contrast-to-noise is calculated by (signal intensity liver—signal intensity tumor) divided by standard deviation of noise. As shown by the imaging, the block copolymeric contrast agents increase the contrast-to-noise from 5 to 12 pre-contrast to over 50, or by a factor of 5 to 10 with low doses of manganese. The images showed intense hepatic enhancement and appreciable contrast in renal cortex and renal pelvis, indicating renal excretion of the contrast agent as well as hepatic uptake. The agent also caused appreciable cardiac enhancement and the agent is also useful for evaluating cardiac ischemia.

Example 11
Synthesis of Gadolinium-Dysprosium Poly-1,5-di-( 2,2'-ethylenedioxydiethyleneiminocarbonylmethylene)- 1,3,5-triazapentane-1,2,5-triacetate (Poly-DTPA-EOEA-Gd-Dy).

Poly-DTPA-EOEA-Gd (4 g) was prepared substantially in accordance with Example 3. Poly-DTPA-EOEA and dysprosium oxide (0.7 g) were then suspended in a reaction vessel and stirred at a temperature between about 80° C. and about 90° C. for about 16 hours. A small amount of undissolved precipitate was then filtered off and the solution evaporated producing 4.5 g of a yellow-white glass-like solid gadolinium-dysprosium containing copolymer (Poly-DTPA-EOEA-Gd-Dy), having a molecular weight of about 60,000.

Example 12
Synthesis of Manganese-Gadolinium Poly-N,N'-di- 2,2'-(ethylenedioxy)-diethyleneiminocarbonylmethyleneethylenediamine-N,N' diacetate-ethylenedioxydiethyleneiminocarbonylmethylene-1,3,5-triazapentane- 1,3,5-triacetate (Poly-DTPA-EDTA-Gd-Mn).

EDTA anhydride (1.28 g) and DTPA anhydride (1.78 g) were mixed with a solution of 2,2'-ethylenedioxydiethylamine (1.48 g) in 200 ml of dried methanol and stirred for 24 hours and then evaporated to dryness yielding 4.5 g of the copolymer poly-DTPA-EDTA-EOEA.

The copolymer Poly-DTPA-EDTA-EOEA (4.5 g) was then dissolved in 100 ml of water, and 0.55 g of manganese carbonate suspended in 10 ml of water was added to the copolymer mixture and stirred at room temperature for 24 hours, at which time most of the manganese carbonate was dissolved. Next, 0.9 g of gadolinium oxide suspended in 10 ml of water was added to the copolymer mixture. The reaction temperature was then raised to about 80° C. for about 16 hours. A small amount of undissolved precipitate was filtered off. The solution was then evaporated to dryness producing 6 g of a yellow glass-like solid manganese-gadolinium containing copolymer (Poly-DTPA-EDTA-EOEA-Gd-Mn), having a molecular weight of about 50,000.

Example 13
Synthesis of Manganese Poly-N-N'-bis- 2,2'-ethylenedioxydiethylenenitrilo-N-($\alpha,\beta$ -dihydroxypropane)-carbonylmethylene-ethylenediamine-N-N' -diacetate-N,N'-bis-ethylene-nitrilo-N-($\alpha,\beta$ -dihydroxypropane-carbonylmethylene-ehtylenediamine-N,N'diacetate (Poly-EDTA-EOEA-DP-EADP-Mn).

N,N'-di-($\alpha,\beta$-dihydroxypropy)-ethylenediamine (EADP) was prepared as follows. In 50 ml of dried methanol, 6 g of ethyldiamine was dissolved and the solution heated to about 60° C. Then, 7.4 g of glycidol was added dropwise, with stirring. The reaction mixture was kept under reflux for 2 hours, and then stirred for one additional hour. The methanol was then evaporated off resulting in 13 g of EA-DP as a viscous liquid.

EOEA-DP was prepared substantially in accordance with Example 7. Poly-EDTA-EOEA-DP-EADP was then prepared as follows. EA-DP (1.34 g) was mixed with EDTA (2.96 g) in 10 ml of dried methanol and stirred for about 8 hours. Then the EOEA-DP in 10 ml of dried methanol was added, and the mixture stirred overnight. The methanol was then evaporated forming 1.1 g of solid copolymer of poly-EDTA-EOEA-DP-EADP.

Poly-EDTA-EOEA-DP-EADP (0.942 g) was next dissolved in 100 ml of water and mixed with 0.224 g of manganese carbonate, and stirred overnight resulting in a transparent reaction mixture. The solution was evaporated to dryness, resulting in 1.1 g of solid copolymer of Poly-EDTA-EOEA-DP-EADP-Mn, having a molecular weight of about 40,000.

Example 14
Synthesis of Manganese Poly-N,N'-bis-2,2'-ethylenedioxy-diethylenenitrilo-N-($\beta$ -cellobiose-$\alpha$-hydroxypropane)carbonylmethylene-ethylenediamine-N,N'-diacetate.

The compound 3-cellobiose-propane-1,2-epoxide was prepared as follows. Cellobiose (3.42 g) was dissolved in 50 ml of ethanol, and 0.56 g of sodium ethoxide in 5 ml of ethanol was added to the solution and stirred for 30 minutes. Next, 1.37 g of 3-bromo-propane-1,2-epoxide and EOEA were refluxed together in dried methanol, substantially following the procedure for EOEA-DP preparation in Example 7 to yield N,N'-di($\beta$ -cellobiose-$\alpha$-hydroxy-propyl-2,2'ethylenedioxy-diethylamine (EOEA-CB).

Poly-EDTA-EOEA-CB was prepared substantially in accordance with the procedure of Poly-EDTA-EOEA-DP preparation in Example 7. Poly-EDTA-EOEA-CB-Mn was then prepared substantially in accordance with the procedure of Poly-EDTA-EOEA-DP-Mn preparation in Example 7, having a molecular weight of about 60,000.

Example 15
Synthesis of Manganese Poly-EDTA-EOEA-DP-Polyethyleneglycol

EOEA-DP (0.296 g) in 10 ml of dried methanol was added to a stirring suspension of EDTA anhydride (0.512 g) in 200 ml of dried methanol, and the mixture was stirred for about 8 hours. Next 8 g of w,w'-diaminopolyethyleneglycol (prepared from polyethyleneglycol of a molecular weight of about 8,000) dissolved in 50 ml of methanol was added to the reaction mixture of EDTA and EOEA-DP, with stirring. Stirring was continued for about 24 hours, resulting in 8.5 g of copolymer. Manganese carbonate (0.23 g) was suspended in a 200 ml solution containing 8.5 g of Poly-EDTA-EOEA-DP-polyethyleneglycol and stirred at about 40° C. for about 16 hours. A small amount of undissolved precipitate was then filtered off. The solution was evaporated to dryness yielding 8.6 g of the yellow-white glass-like copolymer Poly-EDTA-EOEA-DP-polyethyleneglycol, having a molecular weight of about 100,000.

Example. 16
Synthesis of Manganese Poly-EDTA-EOEA-DP-TA

Diethylenetriamine (TA) (1.03 g) and EDTA anhydride (7.68 g) were mixed in 100 ml of dried methanol and stirred for about 5 hours. Concurrently, EOEA-DP (8 g) and EDTA anhydride (7.68 g) were mixed in 100 ml of dried methanol and stirred for about 5 hours. The two mixtures were then mixed together and stirred over-night at room temperature yielding 24 g of a branched star-shaped copolymer, Poly-EDTA-EOEA-DP-TA.

The branched star-shaped copolymer (12 g) was then dissolved in 250 ml of water and mixed with 1.7 g of manganese carbonate and stirred at about 40° C. for about 16 hours. A small amount of undissolved precipitate was then filtered off. The solution was evaporated to dryness producing 12.8 g of a yellow-white glass-like branched star-shaped copolymer poly-EDTA-EOEA-DP-TA, having a molecular weight of about 60,000.

The following Examples 17 and 18 are prophetic examples of the synthesis of targeted copolymeric agents, to illustrate some the labelling of copolymeric contrast agents for specific targeting.

Example 17
Labelling of Poly-EDTA-EOEA-Mn with a Monoclonal Antibody

Poly-EDTA-EOEA-Mn (0.1 g) is synthesized substantially in accordance with Example 2, to a molecular weight of about 3,000, and is dissolved in 10 ml of dimethylsulfoxide (DMSO). To the mixture is then added 1 g of monoclonal antibody (MAb) dissolved in 200 ml of DMSO at a temperature of about 0° C. Next, 0.1 g of DCC in 10 ml of DMSO is added dropwise, and stirred at about 0° C. for about 30 minutes, then at about 20° C. for about 8 hours, and finally at about 50° C. for about 30 minutes. The mixture is then diluted with 200 ml of water and the precipitate of dicyclohexyl urea is filtered off. The resulting aqueous solution is passed through an anionic chromatography column and washed with water (buffered to pH 7.0), yielding Poly-EDTA-EDTA-EOEA-MAb-Mn.

Example 18
Labelling of Poly-EDTA-EOEA-Mn with the Polysaccharide Dextran

Poly-EDTA-EOEA-Mn is synthesized substantially in accordance with Example 2, to a molecular weight of approximately 3,000, and is dissolved in 10 ml of DMSO and mixed with 1 g of finely ground dextran suspended in 100 ml of DMSO. To this is added 0.1 g of DCC with 5 mg of p-dimethylaminopyridine in 5 ml of DMSO and stirred overnight at about 0° C. and then at about 40° C. for about 1 hour. The mixture is then diluted with 200 ml of water and the precipitate of dicyclohexyl urea is filtered off. The resulting solution is then passed through an anionic column and washed with water (buffered to pH 7.0), yielding Poly-EDTA-EOEA-Dextran-Mn.

Various modifications of the invention in addition to those shown and described herein, such as other novel compounds, or other novel compound and paramagnetic ion combinations, or other novel uses thereof, will be apparent to those skilled in the art from the foregoing description. Such modifications are also intended to fall within the scope of the appended claims.

What is claimed is:

1. A method of providing an image of an internal region of a patient comprising
   (i) administering to the patient a compound comprising a copolymer which comprises
      at least two of a first monomer of the formula $X_1-[(CHR_2)_m-CHR_2CHR_2-Y]_n-(CHR_2)_m-CHR_2CHR_2-X_2$, wherein
      $X_1$ and $X_2$ are SH,
      Y is O, NH, $NR_1$, S or CO,
      each Z is, independently, Cl, Br or I,
      n is 0–10,000,
      each m is 0 or 1,
      each $R_1$ is, independently, a $C_1-C_{20}$ substituted or unsubstituted alkyl or cycloalkyl group, and
      each $R_2$ is, independently, H or OH, and
      at least one of a second monomer which is a polynitrilo chelating agent having at least two COOH, $COOR_1$ or COZ groups,
      said first and second monomers bound to one another to form a copolymer through a carboxylic thioester linkage of at least one of said SH groups of said first monomer and at least one of said COOH, $COOR_1$ or COZ groups of said second monomer,
      wherein said first and second monomers comprise at least about 10 monomers;
      and further comprising a paramagnetic ion chelated to said compound; and
   (ii) scanning the patient using magnetic resonance imaging to obtain visible images of the region.

2. A method according to claim 1 wherein said first and second monomers comprise at least about 100 monomers.

3. A method of providing an image of an internal region of a patient comprising
   (i) administering to the patient a compound comprising: a copolymer which comprises
      at least two of a first monomer of the formula $X_1-[(CHR_2)_m-CHR_2CHR_2-Y]_n-(CHR_2)_m-CHR_2CHR_2-X_2$, wherein
      $X_1$ and $X_2$ are SH,
      Y is O, NH, $NR_1$, S or CO,
      each Z is, independently, Cl, Br or I,
      n is 0–10,000
      each m is 0 or 1,
      each $R_1$ is, independently, a $C_1-C_{20}$ substituted or unsubstituted alkyl or cycloalkyl group, and
      each $R_2$ is, independently, H or OH, and
      at least one of a second monomer which is a polynitrilo chelating agent having at least two COOH, $COOR_1$ or COZ groups, and
      at least one of a third monomer which is a targeting agent, said targeting agent having an OH, $NH_2$, $NHR_1$, COOH, $COOR_1$, SH or COZ group,
      said first, second and third monomers bound to one another to form a copolymer through a carboxylic thioester linkage of at least one of said SH groups of said first monomer, at least one of said COOH, $COOR_1$ or COZ groups of said second monomer, and at least one of said OH, $NH_2$, $NHR_1$, COOH, $COOR_1$, SH or COZ groups of said third monomer,
      wherein said first, second and third monomers comprise at least about 10 monomers; and further comprising a paramagnetic ion chelated to said compound; and
   (ii) scanning the patient using magnetic resonance imaging to obtain visible images of the region.

4. A method according to claim 3 wherein said first, second and third monomers comprise at least about 100 monomers.

5. A method for diagnosing the presence of diseased tissue in a patient comprising
   (i) administering to the patient a compound comprising a copolymer which comprises
      at least two of a first monomer of the formula $X_1-[(CHR_2)_m-CHR_2CHR_2-Y]_n-(CHR_2)_m-CHR_2CHR_2-X_2$, wherein
      $X_1$ and $X_2$ are SH,
      Y is O, NH, $NR_1$, S or CO,
      each Z is, independently, Cl, Br or I,
      n is 0–10,000,
      each m is 0 or 1,
      each $R_1$ is, independently, a $C_1-C_{20}$ substituted or unsubstituted alkyl or cycloalkyl group, and
      each $R_2$ is, independently, H or OH, and
      at least one of a second monomer which is a polynitrilo chelating agent having at least two COOH, $COOR_1$ or COZ groups,
      said first and second monomers bound to one another to form a copolymer through a carboxylic thioester linkage of at least one of said SH groups of said first monomer and at least one of said COOH, $COOR_1$ or COZ groups of said second monomer, wherein said first and second monomers comprise at least about 10 monomers;

and further comprising a paramagnetic ion chelated to said compound; and (ii) scanning the patient using magnetic resonance imaging to obtain visible images of any diseased tissue in the patient.

6. A method according to claim 5 wherein said first and second monomers comprise at least about 100 monomers.

7. A method for diagnosing the presence of diseased tissue in a patient comprising (i) administering to the patient a compound comprising: a copolymer which comprises at least two of a first monomer of the formula $X_1—[(CHR_2)_m—CHR_2CHR_2—Y]_n—(CHR_2)_m—CHR_2CHR_2—X_2$, wherein $X_1$ and $X_2$ are SH, Y is O, NH, $NR_1$, S or CO, each Z is, independently, Cl, Br or I, n is 0–10,000, each m is 0 or 1, each $R_1$ is, independently, a $C_1$–$C_{20}$ substituted or unsubstituted alkyl or cycloalkyl group, and each $R_2$ is, independently, H or OH, and at least one of a second monomer which is a polynitrilo chelating agent having at least two COOH, $COOR_1$ or COZ groups, and at least one of a third monomer which is a targeting agent, said targeting agent having an OH, $NH_2$, $NHR_1$, COOH, $COOR_1$, SH or COZ group, said first, second and third monomers bound to one another to form a copolymer through a carboxylic thioester linkage of at least one of said SH groups of said first monomer, at least one of said COOH, $COOR_1$ or COZ groups of said second monomer, and at least one of said OH, $NH_2$, $NHR_1$, COOH, $COOR_1$, SH or COZ groups of said third monomer, wherein said first, second and third monomers comprise at least about 10 monomers;

and further comprising a paramagnetic ion chelated to said compound; and (ii) scanning the patient using magnetic resonance imaging to obtain visible images of any diseased tissue in the patient.

8. A method according to claim 7 wherein said first, second and third monomers comprise at least about 100 monomers.

9. A kit for magnetic resonance imaging comprising a compound which comprises a copolymer comprising at least two of a first monomer of the formula $X_1—[(CHR_2)_m—CHR_2CHR_2—Y]_n—(CHR_2)_m—CHR_2CHR_2—X_2$, wherein $X_1$ and $X_2$ are SH, Y is O, NH, $NR_1$, S or CO, each Z is, independently, Cl, Br or I, n is 0–10,000, each m is 0 or 1, each $R_1$ is, independently, a $C_1$–$C_{20}$ substituted or unsubstituted alkyl or cycloalkyl group, and each $R_2$ is, independently, H or OH, and at least one of a second monomer which is a polynitrilo chelating agent having at least two COOH, $COOR_1$ or COZ groups, said first and second monomers bound to one another to form a copolymer through a carboxylic thioester linkage of at least one of said SH groups of said first monomer and at least one of said COOH, $COOR_1$ or COZ groups of said second monomer, wherein said first and second monomers comprise at least about 10 monomers; and further comprising a paramagnetic ion chelated to said compound.

10. A kit according to claim 9 wherein said first and second monomers comprise at least about 100 monomers.

11. A kit for magnetic resonance imaging comprising a compound which comprises: a copolymer comprising at least two of a first monomer of the formula $X_1—[(CHR_2)_m—CHR_2CHR_2—Y]_n—(CHR_2)_m—CHR_2CHR_2—X_2$, wherein $X_1$ and $X_2$ are SH, Y is O, NH, $NR_1$, S or CO, each Z is, independently, Cl, Br or I, n is 0–10,000, each m is 0 or 1, each $R_1$ is, independently, a $C_1$–$C_{20}$ substituted or unsubstituted alkyl or cycloalkyl group, and each $R_2$ is, independently, H or OH, and at least one of a second monomer which is a polynitrilo chelating agent having at least two COOH, $COOR_1$ or COZ groups, and at least one of a third monomer which is a targeting agent, said targeting agent having an OH, $NH_2$, $NHR_1$, COOH, $COOR_1$, SH or COZ group, said first, second and third monomers bound to one another to form a copolymer through a carboxylic thioester linkage of at least one of said SH groups of said first monomer, at least one of said COOH, $COOR_1$ or COZ groups of said second monomer, and at least one of said OH, $NH_2$, $NHR_1$, COOH, $COOR_1$, SH or COZ groups of said third monomer, wherein said first, second and third monomers comprise at least about 10 monomers; and further comprising a paramagnetic ion chelated to said compound.

12. A kit according to claim 11 wherein said first, second and third monomers comprise at least about 100 monomers.

13. A kit according to claim 9 further comprising conventional magnetic resonance imaging kit components.

14. A kit according to claim 10 further comprising conventional magnetic resonance imaging kit components.

15. A kit according to claim 11 further comprising conventional magnetic resonance imaging kit components.

16. A kit according to claim 12 further comprising conventional magnetic resonance imaging kit components.

* * * * *

UNITED STATES PATENT AND TRADEMARK OFFICE
CERTIFICATE OF CORRECTION

PATENT NO. : 5,517,993
DATED : May 21, 1996
INVENTOR(S) : Evan C. Unger et al.

It is certified that error appears in the above-indentified patent and that said Letters Patent is hereby corrected as shown below:

In column 1, line 7, please delete "Sept. 14," and insert --Sept. 13,-- therefor.

In column 1, line 7, please delete "5,453,127" and insert --5,458,127-- therefor.

In column 2, line 18, please delete "*AJB*," and insert --*AJR*,-- therefor.

In column 3, line 14, please delete "$R_3$" and insert --$R_2$-- therefor.

In column 6, line 27, please delete "and" and insert --are-- therefor.

In column 6, line 49, please delete "dimethyll,3-propanediol," and insert --dimethyl-1,3-propanediol,-- therefor.

In column 8, line 57, please delete "1,3,5'-triazapentane-1,3,5-triacetate," and insert --1,3,5-triazapentane-1,3,5-triacetate,-- therefor.

In column 13, line 15, please delete "St," and insert --Sr-- therefor.

UNITED STATES PATENT AND TRADEMARK OFFICE
CERTIFICATE OF CORRECTION

PATENT NO. : 5,517,993
DATED : May 21, 1996
INVENTOR(S) : Evan C. Unger et al.

It is certified that error appears in the above-indentified patent and that said Letters Patent is hereby corrected as shown below:

In column 22, line 49, please delete "Signal Intensity" from both the second and third columns.

In column 22, line 51, please insert --Signal Intensity-- in both the second and third columns.

In column 23, line 9, please delete "and the", and insert --and thus the-- therefor.

Signed and Sealed this

Twenty-ninth Day of October 1996

Attest:

BRUCE LEHMAN

Attesting Officer

Commissioner of Patents and Trademarks